US007503890B2

(12) United States Patent
Kubicsko et al.

(10) Patent No.: US 7,503,890 B2
(45) Date of Patent: Mar. 17, 2009

(54) COLLAPSIBLE PATIENT ISOLATION POD

(75) Inventors: Stephen Kubicsko, Westminster, MD (US); Peter J. Cooper, North Potomac, MD (US); John Buchanan, University Place, WA (US)

(73) Assignee: TVi Corporation, Glenn Dale, MD (US)

( * ) Notice: Subject to any disclaimer, the term of this patent is extended or adjusted under 35 U.S.C. 154(b) by 217 days.

(21) Appl. No.: 11/452,189

(22) Filed: Jun. 13, 2006

(65) Prior Publication Data

US 2007/0056593 A1    Mar. 15, 2007

Related U.S. Application Data

(60) Provisional application No. 60/690,034, filed on Jun. 13, 2005.

(51) Int. Cl.
*A61G 10/00* (2006.01)
(52) U.S. Cl. .................................................. 600/21
(58) Field of Classification Search ............... 600/20, 600/21; 128/205.26; 312/1, 3, 209; 135/97
See application file for complete search history.

(56) References Cited

U.S. PATENT DOCUMENTS

| 3,492,987 | A | | 2/1970 | Parker | |
|---|---|---|---|---|---|
| 4,129,122 | A | | 12/1978 | Dout et al. .................. | 128/1 R |
| 4,224,936 | A | | 9/1980 | Cox | |
| 4,335,712 | A | | 6/1982 | Trexler | |
| 4,790,051 | A | | 12/1988 | Knight ........................ | 27/28 |
| 4,922,562 | A | | 5/1990 | Allred et al. ................ | 5/82 R |
| 4,950,222 | A | * | 8/1990 | Scott et al. .................. | 600/21 |
| 5,020,546 | A | | 6/1991 | Russo ........................ | 128/849 |
| 5,061,235 | A | | 10/1991 | Hogan ........................ | 600/21 |
| 5,074,894 | A | | 12/1991 | Nelson ........................ | 55/210 |
| 5,152,814 | A | | 10/1992 | Nelson ........................ | 55/270 |
| 5,314,377 | A | | 5/1994 | Pelosi, III .................... | 454/187 |
| 5,342,121 | A | * | 8/1994 | Koria ........................... | 312/1 |
| 5,533,305 | A | | 7/1996 | Bielecki ...................... | 52/79.1 |
| 5,626,151 | A | | 5/1997 | Linden ........................ | 128/897 |
| 5,728,041 | A | | 3/1998 | Fowler, Jr. | |
| 5,950,625 | A | | 9/1999 | Bongiovanni et al. ....... | 128/845 |
| 5,975,081 | A | | 11/1999 | Hood et al. .................. | 128/845 |

(Continued)

*Primary Examiner*—Samuel G Gilbert
(74) *Attorney, Agent, or Firm*—Whiteford, Taylor & Preston LLP; Jeffrey C. Maynard; Gregory M. Stone

(57) ABSTRACT

A collapsible patient isolation pod for preventing flow of contaminants to or from a patient is disclosed. The isolation pod is preferably fabricated at least partially from a transparent, biochemically resistive material and includes a flexible enclosure that is configurable to receive a contaminated patient therein. The top is maintained spaced apart from the bottom such that the top is maintained out of physical contact with a contaminated patient received in the enclosure. The isolation pod has a plurality of wide, gloved access points to allow easy, multiple access points to a patient. A central connection manifold for oxygen, intravenous connections, or other fluids, may optionally be provided. Ventilation is provided within the isolation chamber with a negative pressure ventilation system and filtration on the air input near the patient's head, and provides filtration on output near the patient's feet. An integral pocket underneath the isolation pod may be provided to allow for a spine board or stretcher to be used. The invention provides a patient isolation system that permits health care providers safe and relatively unencumbered access to the isolated patient.

79 Claims, 6 Drawing Sheets

U.S. PATENT DOCUMENTS

| | | | |
|---|---|---|---|
| 6,217,507 B1 | 4/2001 | Bonvik | 600/21 |
| 6,241,653 B1 * | 6/2001 | Gauger et al. | 600/21 |
| 6,321,764 B1 | 11/2001 | Gauger et al. | 135/128 |
| 6,418,932 B2 | 7/2002 | Paschal, Jr. et al. | 128/845 |
| 6,461,290 B1 * | 10/2002 | Reichman et al. | 600/21 |
| 6,969,346 B2 * | 11/2005 | Perlatti | 600/21 |
| 6,971,985 B2 | 12/2005 | Perlatti | |
| 6,997,483 B2 | 2/2006 | Perlatti | |
| 2002/0133100 A1 * | 9/2002 | Paschal et al. | 601/16 |
| 2004/0074212 A1 | 4/2004 | Yachi et al. | 55/385.2 |
| 2004/0111007 A1 | 6/2004 | Perlatti | 600/21 |
| 2004/0111008 A1 | 6/2004 | Perlatti | 600/21 |
| 2004/0215051 A1 | 10/2004 | Perlatti | 600/21 |
| 2004/0239107 A1 | 12/2004 | Perlatti | 285/117 |

* cited by examiner

COLLAPSIBLE PATIENT ISOLATION POD

CROSS REFERENCE TO RELATED APPLICATION

This application is based upon and claims benefit of and co-owned U.S. Provisional Patent Application Ser. No. 60/690,034 entitled "Collapsible Patient Isolation Pod", filed with the U.S. Patent and Trademark Office on Jun. 13, 2005 by the inventors herein, the specification of which is incorporated herein by reference.

BACKGROUND OF THE INVENTION

1. Field of the Invention

This invention relates generally to an isolation system for transporting a patient, and more particularly to a system and method for protecting the patient against exposure to a hazardous environment, and protecting persons aiding the patient against contamination from the patient.

2. Background of the Prior art

Typically, when a person is injured and becomes a victim in a contaminated environment, such as occurs in a chemical warfare confrontation, the victim is placed within an enclosure for transportation to a medical facility. Ideally, the enclosure is manufactured of a material that inhibits or prevents the transfer of contaminants from the ambient environment to the victim and from the victim to caregivers, such as medical personnel.

In many cases, it is imperative that medical treatment be given to the patient immediately. However, in order to administer treatment, it is preferred that the patient be isolated and transported into an enclosure within which medical personnel may work on the patient, or additional means must be provided for allowing access to the patient without introducing contaminants into the enclosure containing the patient and without risking contamination of the medical personnel. In this regard, it is desirable to isolate the patient from the environment when the environment contains substances that may be detrimental to the medical patient. For example, if the patient has suffered severe blood loss or is experiencing difficulty breathing, then it is desirable to prevent the patient from breathing dust, engine exhaust, smoke, etc. It is also desirable to isolate the medical patient from the environment when bacteriological, chemical and/or radiological hazards are present, as may occur during battlefield conditions. Similarly, it is desirable to isolate a contaminated patient to ensure that such contamination is not spread to the medical personnel providing treatment.

There are many devices and structures available in the art for isolating a patient for protection against additional exposure to a hazardous environment while monitoring the patient as well as isolating the potentially infectious patient from caregivers to prevent exposure and/or contamination. Many such devices are directed to use with an individual patient who is exposed to ambient contamination from, for example, chemical, biological, infectious agent, environmental, and radiation sources.

Unfortunately, prior art apparatuses currently available for treating the patient in the field are generally ineffective in providing an environment conducive to the administration of medical treatment, and can thus cause treatment to be delayed until the patient is transported to an adequate medical facility, which is frequently not readily accessible. Such prior art apparatuses are further generally deficient in providing an environment where both the patient and medical personnel treating the patient are protected from contaminants, let alone actually facilitate the removal of contaminants already present on the skin and/or clothes of the casualty victim.

SUMMARY OF THE INVENTION

Disclosed is a collapsible patient isolation pod that provides protection against further contamination of the patient, and against cross contamination of the surrounding environment to allow transport of victims from an incident scene to a more advanced medical treatment facility with a minimum of risk to the healthcare provider. With reference to a particularly preferred embodiment, a plurality of flexible arches along the length of the isolation pod supports a vinyl enclosure above the patient and provides a voluminous work/patient space. The isolation pod has a plurality of wide, gloved access points to allow easy, multiple access points to a patient. A negative pressure ventilation system provides filtration on the air input, preferably situated near the patient's head, and also provides filtration on output, preferably situated near the patient's feet to prevent recontamination of the patient while providing longitudinal airflow. A snorkel is provided to enable wires or tubes to be connected inside the enclosure while maintaining a seal from the environment. Optionally, a central push/pull connection manifold for oxygen, intravenous connections, or other fluids, enables quick and simple connect/disconnects with self-closing internal valves. One or more service sleeves may be provided to enable materials and equipment to be passed into or out of the enclosure while maintaining a seal from the environment. Several wide belts with handgrips may be provided on each side to enable staff to transport and safely maneuver a patient in the isolation pod. Likewise, straps may be provided to enable attachment of the isolation pod to a stretcher or gurhey. Internal restraint straps may also be provided to hold a patient securely within the isolation pod. An optional integral pocket can be provided on the bottom of the isolation pod to allow for a spine board or stretcher to be used in combination with the isolation pod. The isolation pod provides a patient isolation system that permits health care providers relatively unencumbered access to the isolated patient.

In some embodiments, an isolation pod is provided to supply an emergency, short-term, single patient, isolation pod utilizing lightweight materials and airtight sealing. The isolation pod can be constructed of materials that allow it to be decontaminated after use yet can be easily stored and quickly set up.

In a particularly preferred embodiment of the invention, an isolation pod is provided having a negative pressure, filtered ventilation air system that stays clean and can be re-used. The ventilation system should be easily configurable and use replaceable parts.

The various features of novelty that characterize the invention will be pointed out with particularity in the claims of this application.

BRIEF DESCRIPTION OF THE DRAWINGS

The above and other features, aspects, and advantages of the present invention are considered in more detail, in relation to the following description of embodiments thereof shown in the accompanying drawings, in which.

DETAILED DESCRIPTION OF EXEMPLARY EMBODIMENTS

Figure 1:
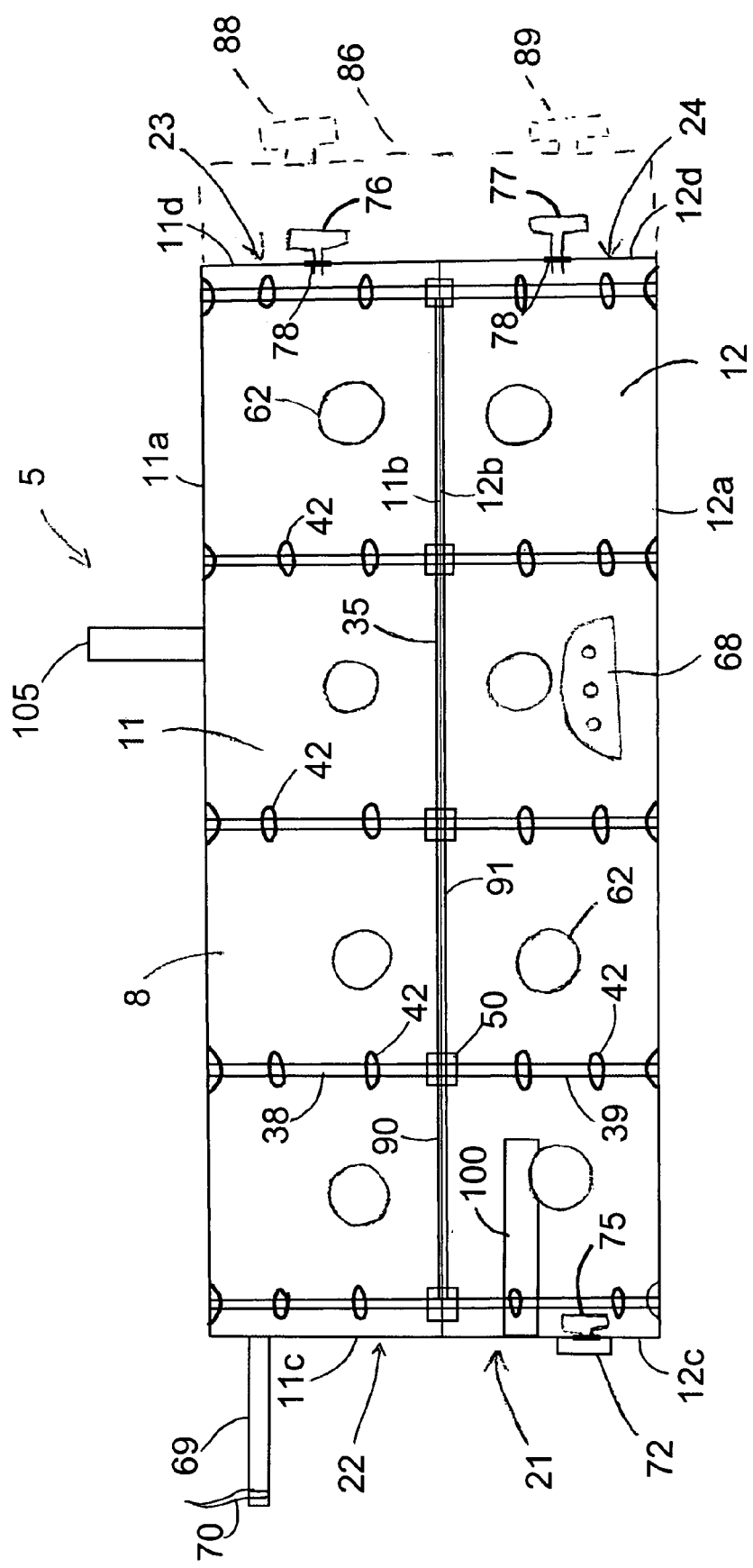
FIG. 1 shows a plan view of an isolation pod according to a particularly preferred embodiment of the present invention.
Figure 2:
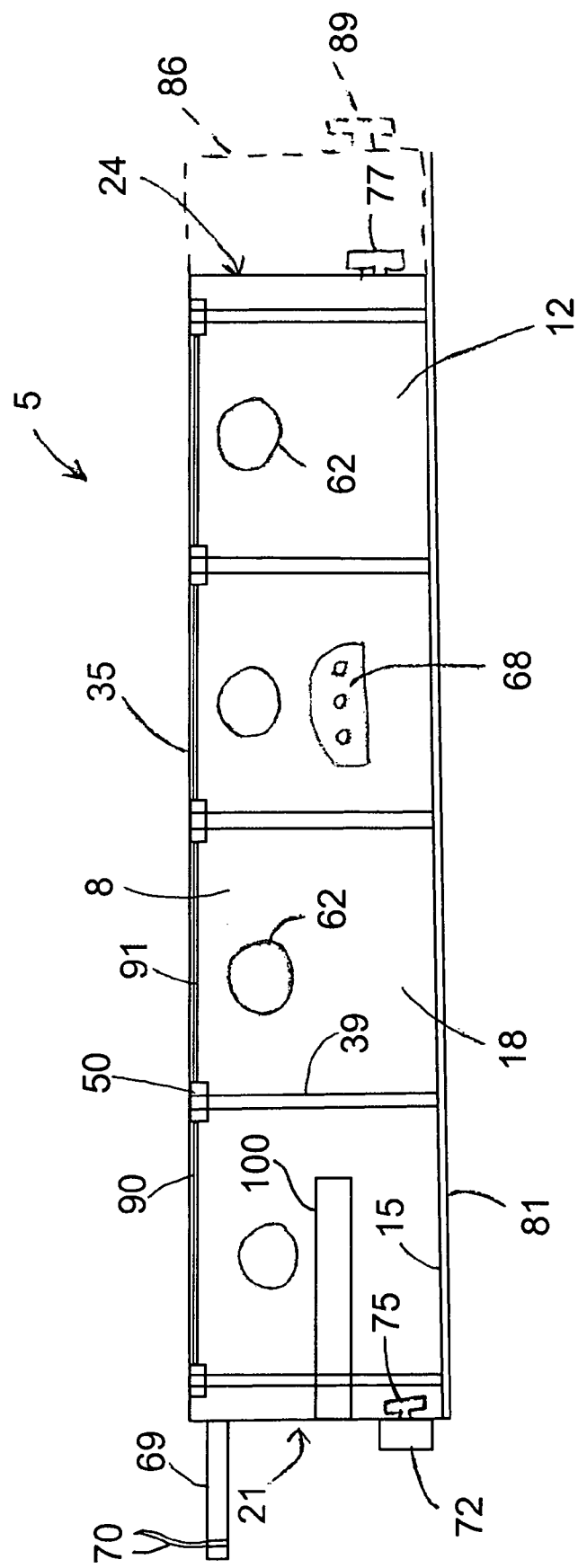
FIG. 2 shows a side elevational view of the isolation pod of FIG. 1.

The invention summarized above and defined by the enumerated claims may be better understood by referring to the following description, which should be read in conjunction with the accompanying drawings in which like reference numbers are used for like parts. This description of an embodiment, set out below to enable one to build and use an implementation of the invention, is not intended to limit the enumerated claims, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

Referring to the drawings, FIGS. 1-4 show an isolation pod, indicated generally as 5, according to a first preferred embodiment of the invention. The isolation pod 5 comprises an enclosure 8 of suitable length having a left portion 11, a right portion 12, and a base sheet 15 forming a main chamber 18 that is preferably sized to receive an average-sized person therein. The left portion 11 and right portion 12 are substantially rectangular shaped, having two long sides, such as 11a, 11b, 12a, and 12b, respectively, and two short sides, such as 11c, 11d, 12c, and 12d, respectively, and are attached on one of the long sides 11a, 12a to the base sheet 15 by appropriate means, such as sewing, or ultrasonic or radio frequency (RF) welding. Base sheet 15 is likewise substantially rectangular shaped. In use, and by way of non-limiting example, the isolation pod 5 may measure approximately 76-inches long by approximately 27-inches wide by approximately 17-inches high. The enclosure 8 is suitably made from a flexible chemical-resistant material such as 16-gage polyvinyl chloride (PVC) that is heavy duty and puncture resistant. However, it will be appreciated that any thickness of material may be selected as desired for a particular application. Further, the enclosure 8 may be made from material, either in its entirety or in portions thereof, that can be seen through, such as clear vinyl or clear or colored PVC. This permits a contaminated patient in the main chamber 18 to see outside the enclosure 8 and permits the patient to be seen by medical care providers and other people outside the enclosure 8.

Figure 3:
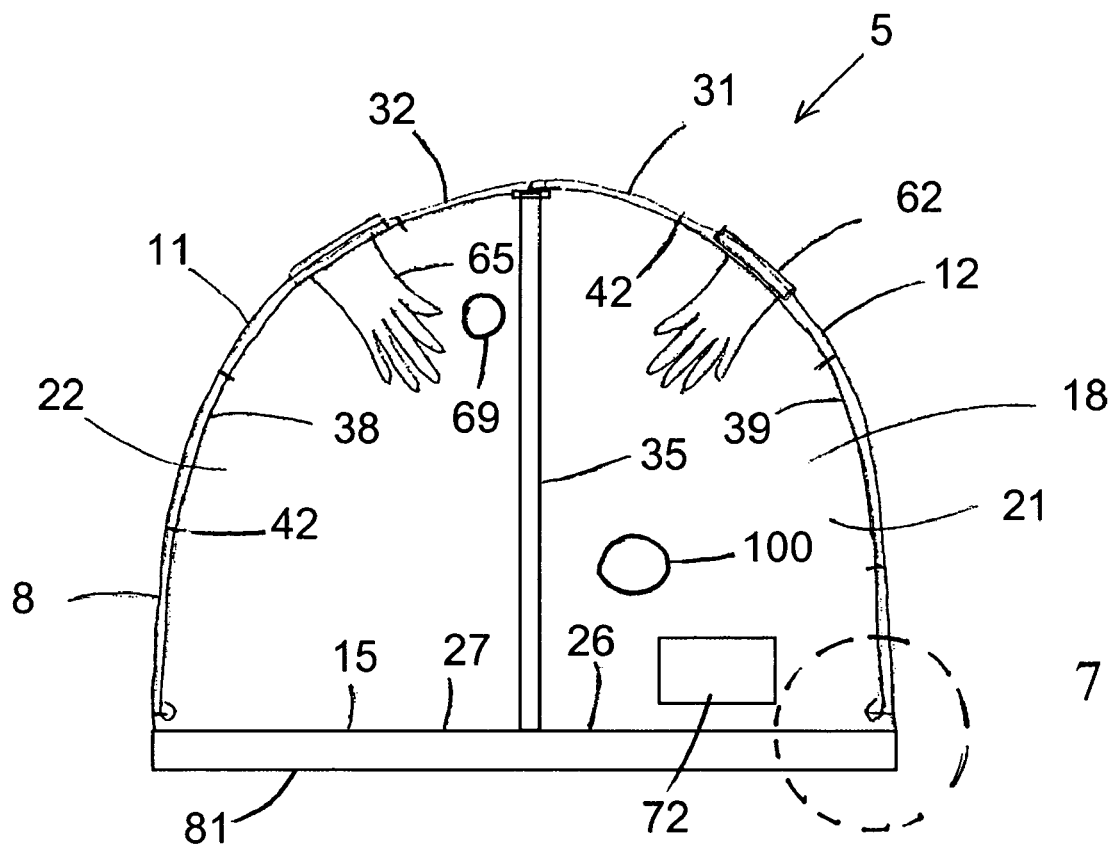
FIG. 3 shows an end elevational view of the isolation pod of FIG. 1.

End panels 21, 22, 23, 24 are substantially shaped as a quarter of a circle and attached at a bottom edge, such as 26, 27 shown in FIG. 3, to the base sheet 15 by suitable means. The curved portion, such as 31, 32 shown in FIG. 3, of the end panels 21, 22 is attached to the short sides 11c, 12c of left and right portions 11, 12. In a similar manner, the curved portion of end panels 23, 24 is attached to the short sides 11d, 12d of left and right portions 11, 12. The remaining long side 11b, 12b of left and right portions 11, 12 and the remaining side of end panels 21, 22, 23, 24 are provided with a closure mechanism, such as hook-and-loop closures or a sealed zipper seam 35.

A lightweight support frame is preferably established by the placement of a plurality of flexible ribs, such as 38, 39, each preferably passed through a plurality of guide loops 42 formed at select locations on the interior of the left and right portions 11, 12. By way of non-limiting example, the ribs 38, 39 are preferably approximately 1-inch wide by approximately 14-inch thick by approximately 27-inches long. Other sizes can be used. The length of the ribs is selected such that it will not extend over the edge of the base sheet 15 in the folded, storage configuration.

Figure 5:
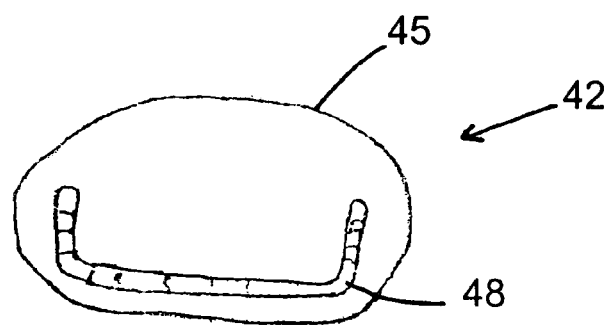
FIG. 5 shows a frontal view of a guide loop mechanism for use with the isolation pod of FIG. 1.

Referring to FIG. 5, the guide loops 42 comprise a back portion 45 and a rigid ring portion 48. The guide loops 42 are integrally formed on or anchored to the interior of the left and right portions 11, 12 by heat sealing, adhesives, or other conventional techniques. The ribs 38, 39 are slidably engaged in the guide loops between the ring portion 48 and the back portion 45.

Figure 6:
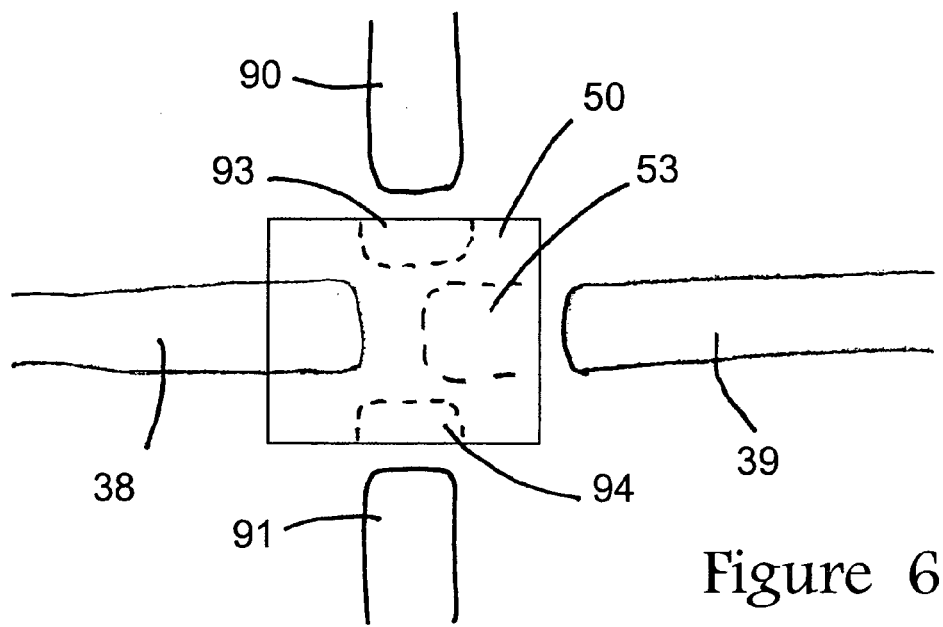
FIG. 6 shows an illustration of a rib connecting mechanism for use with the isolation pod of FIG. 1.

As shown in FIG. 6, a connecting housing 50 is provided to releasably join oppositely deployed ribs. The connecting housing 50 is suitably made of plastic or nylon approximately 3-inches long by approximately 2-inches wide by approximately ¾-inch thick. Other sizes can be used and one skilled in the art will select appropriate sizes for the ribs 38, 39 and the connecting housing 50. Each rib 38, 39 is slidably engaged with a slot 53 provided on opposite sides of connecting housing 50. Slots 53 are sized and configured to enable ribs 38, 39 to slidably engage therein. Optionally, one or more rib members 38 and 39 may be rigidly attached to connecting housing 50.

In a preferred embodiment, a plurality of flexible spines, such as 90, 91, may be operatively engaged between adjacent ribs 38, 39 to provide longitudinal stability. Slots 93, 94 may be provided on opposite sides of connecting housing 50, sized and configured to enable spines 90, 91 to slidably engage therein. The longitudinal spines 90, 91 are sized and configured to extend between adjacent connecting housings 50 in the support frame. When the isolation pod 5 is closed, the longitudinal spines 90, 91 are preferably positioned directly under the closure seam 35.

Figure 7A:
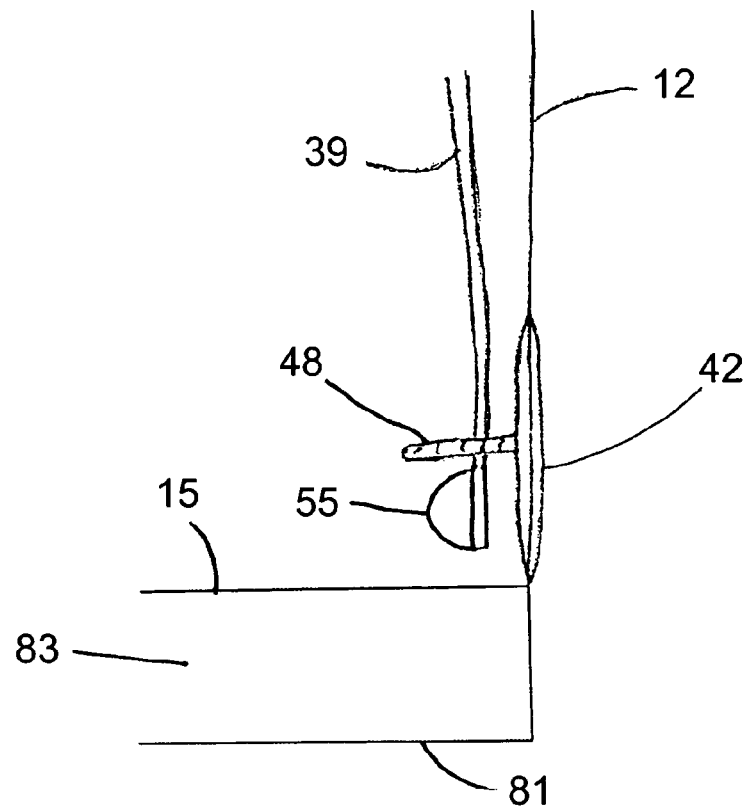
FIGS. 7a and 7b shows an enlarged portion of FIG. 3, illustrating a rib attachment mechanism for use with the isolation pod of FIG. 1.
Figure 7B:
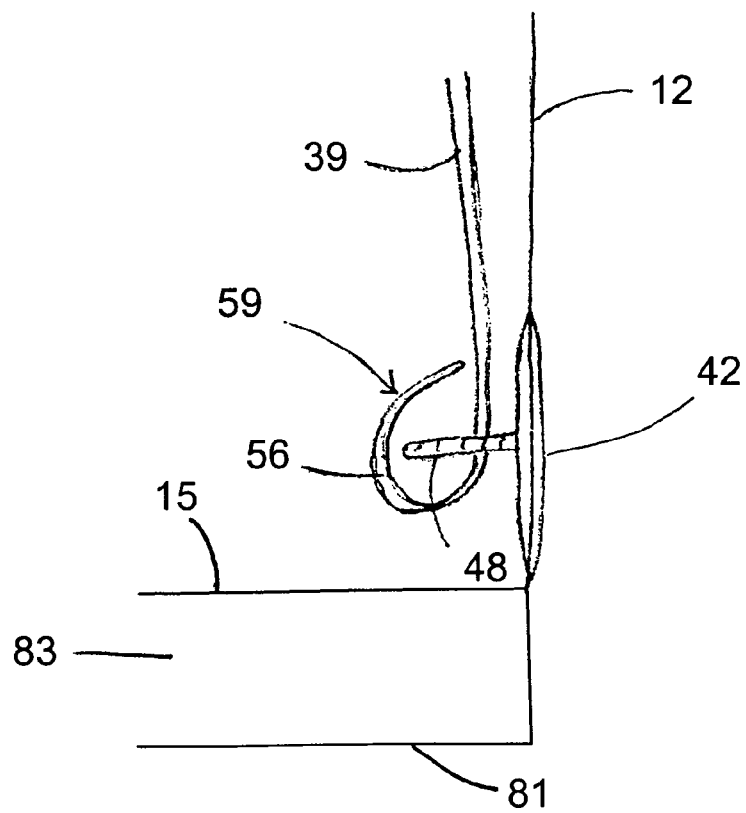

FIGS. 7a and 7b illustrate alternate arrangements of rib attachment mechanisms. In FIG. 7a, rib 39 is provided with a detent 55 on its lower end. The detent 55 is sized and configured to enable the lower end of rib 39 to be slid between the ring portion 48 and the back portion 45 of guide loop 42 and releasably held in place. The detent 55 prevents removal of the rib 39 at least during normal use. The guide loop 42 should be the lower most guide loop on the left and right portions 11, 12. FIG. 7b shows an optional alternate configuration. Rib 39 may be hingedly attached to the ring portion 48 of guide loop 42. A lower part 56 of rib 39 is curved around the ring portion 48 to form a hook 59 that can rotate about ring portion 48.

It is preferred to deploy the supporting flexible ribs, such as 38, 39, and spines 90, 91 on the inside of the isolation pod 5. Due to evacuation of air from the interior of the main chamber 18, a negative pressure is developed, which would tend to collapse an unsupported enclosure 8 about a patient sealed therein. Consequently, the use of a supporting frame is desirable.

To open the enclosure 8, the sealed zipper seam 35 (FIG. 1) is opened and the left and right portions 11, 12 are splayed open by preferably sliding the PVC material and guide loops 42 into an open position along ribs 38, 39. The end panels 21, 22, 23, 24, being connected to their respective left and right portions 11 and 12 are likewise folded toward the side of the enclosure 8. Spines 90, 91 may be removed from the connecting housing 50. One or more of ribs 38, 39 then may be removed from the connecting housing 50, and ribs 38, 39 may be pivoted outward from the main chamber 18. To configure the isolation pod 5 for storage, the PVC material is extended onto the ribs 38, 39 without the ribs being connected in the connecting housing 50. Ribs 38, 39 and each of the left and right portions 11, 12 are laid flat onto the base sheet 15 and the isolation pod 5 can be folded into a storage box, bag or the like. The ribs 38, 39 need not be removed from the guide loops 42. The spines are disconnected from the connecting housing 50 and also laid flat onto the base sheet 15 to be folded in for storage.

To further facilitate caregiver activities such as decontamination, cleaning, airway management, and the like, the enclosure 8 includes a plurality of glove ports 62 having tear resistant gloves 65 of conventional construction and composition. The gloves 65 are sealed to the enclosure 8 by means of, for example, a cam and groove ring that is known in the art. When glove ports 62 are fitted with gloves 65, an operator standing outside of the enclosure 8 is able to manipulate the contents within the main chamber 18. The gloves 65 are of pliable, chemical-resistant material, such as latex or other material used in the biohazards industry. The gloves 65 include a reinforced portal and tubular sleeves to allow for patient treatment without exposure of the patient to the environment outside of the enclosure 8, or exposure of caregivers to contaminants on the patient. Alternatively, when it is desired to perform an intricate medical procedure, such as an autopsy within the main chamber 18, surgical-quality or examination-quality gloves are preferably used.

Optionally, a centrally located manifold 68 may be disposed on at least one of the left and right portions 11, 12. The manifold 68 comprises a plurality of push/pull connections having self-closing internal valves to enable air, oxygen, intravenous connections, or other fluids to be administered to a patient within the enclosure 8. It may further permit wires for monitoring devices, such as an electrocardiogram, or devices for monitoring other vital signs to be connected to the contaminated patient. Each push/pull connection has a fitting on the outside of the manifold for attaching a tube or the like. On the inside, a similar fitting enables a tube to attach to the manifold 68 inside the enclosure 8. The push/pull connections are designed to have an internal seal when the connection is pushed in. Once a tube or other connection is attached, the fitting is pulled out to open the internal seal. The manifold 68 enables quick and simple connect/disconnect of tubes and other lines. In a preferred embodiment, the internal seal permits flow in only one direction.

In a preferred embodiment, a hollow snorkel 69 may be provided on at least one of end panels 21, 22, 23, 24. The snorkel 69 enables passage of tubes for intravenous or oxygen lines and/or wires for monitoring devices or powered equipment into the interior of chamber 18. A strap 70 is used to seal the snorkel 69. Strap 70 may include hook-and-loop fasteners to seal upon itself and maintain the snorkel 69 closed.

The interior of enclosure 8 is usually maintained at a negative pressure through use of at least one fan 72 that pulls a suction on the main chamber 18 through a high efficiency filter 75, which is located within the chamber 18. Such filter 75 may be a HEPA filter for filtering particulate, an OVAG filter for filtering organic vapor, acid, or gas, or combinations of HVAC and OVAG. In a preferred embodiment, a long-life battery 73 (FIG. 4) powers fan 72. The battery 73 is preferably a Lithium polymer rechargeable battery or a Nickel-Cadmium rechargeable battery, and is preferably removably held on an outer wall of one of end panels 21, 22, 23, 24, such as by use of a hook-and-loop fastener arrangement. Other types of batteries can be used. A charging port for the battery 73 may also be provided.

Figure 8:
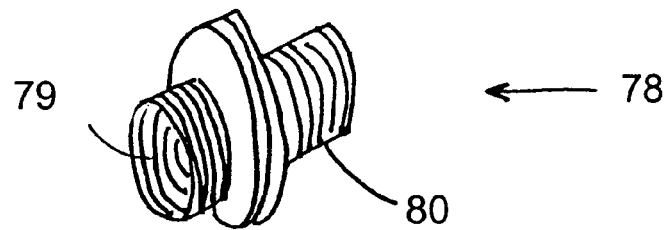
FIG. 8 shows an illustration of a wall fitting for use with the isolation pod of FIG. 1.

Air is allowed to enter the main chamber 18 through one or more high efficiency filters 76, 77, which are located outside the enclosure 8. Filters 76, 77 decontaminate the air entering the main chamber 18 and filter 75 decontaminates the air exiting the chamber 18. Various types and numbers of filters can be used. Fan 72 and filters 75, 76, 77 are connected to the isolation pod 5 through a wall fitting 78, such as shown in FIG. 8. Wall fitting 78 is designed to have internal threads 79, on the inside of the wall fitting 78 for receiving externally threaded components, such as a filter. The wall fitting 78 also has external threads 80, on the outside of the fitting 78 for receiving internally threaded components, such as a hose, a fan assembly, or other component.

Fan 72 is preferably sized to enable airflow of approximately 3-6 cubic feet per minute (CFM) through the main chamber 18, which will enable the air to be changed in the chamber 18 approximately twelve times per hour. In a particularly preferred embodiment, airflow monitors (not shown) may track the turnover rate of air within chamber 18. When a patient is in the main chamber 18, it is preferred that airflow, providing ventilation inside the chamber 18, enters the chamber 18 near the patient's head and exits near the patient's feet in such a manner that it enables refreshed air to pass through the chamber 18 and washes over the patient in a head-to-toe direction such that rapid removal of toxic and infectious residues is facilitated. This further minimizes potential contamination of the patient's respiratory system and helps to cool and relax the patient. In some embodiments, a respirator unit, such as a powered air purifying respirator or pressurized source of clean air can be connected directly to the main chamber 18 at any of the wall fittings 78.

In some embodiments, the ventilation can be configured to create a positive pressure environment inside the enclosure 8 for burn patients or other immune compromised patients.

Bottom sheet 15 may be constructed of any appropriate material that can be attached to the left and right portions 11, 12 and the end panels 21, 22, 23, 24. The bottom sheet 15 should be, at least, waterproof and may be reinforced. Optionally, a second bottom sheet 81 (FIG. 2), having substantially the same shape and size as bottom sheet 15 may be disposed under the bottom sheet 15 and attached only along the long sides of the bottom sheets 15 and 81, thus forming a sleeve 83 that is open on the short side ends of the isolation pod 5. The sleeve 83 enables a spine board or stretcher (not shown) to be inserted therein, between the bottom sheet 15 and the second bottom sheet 81. The spine board or stretcher may provide rigidity for transporting a patient in the isolation pod 5.

Figure 4:
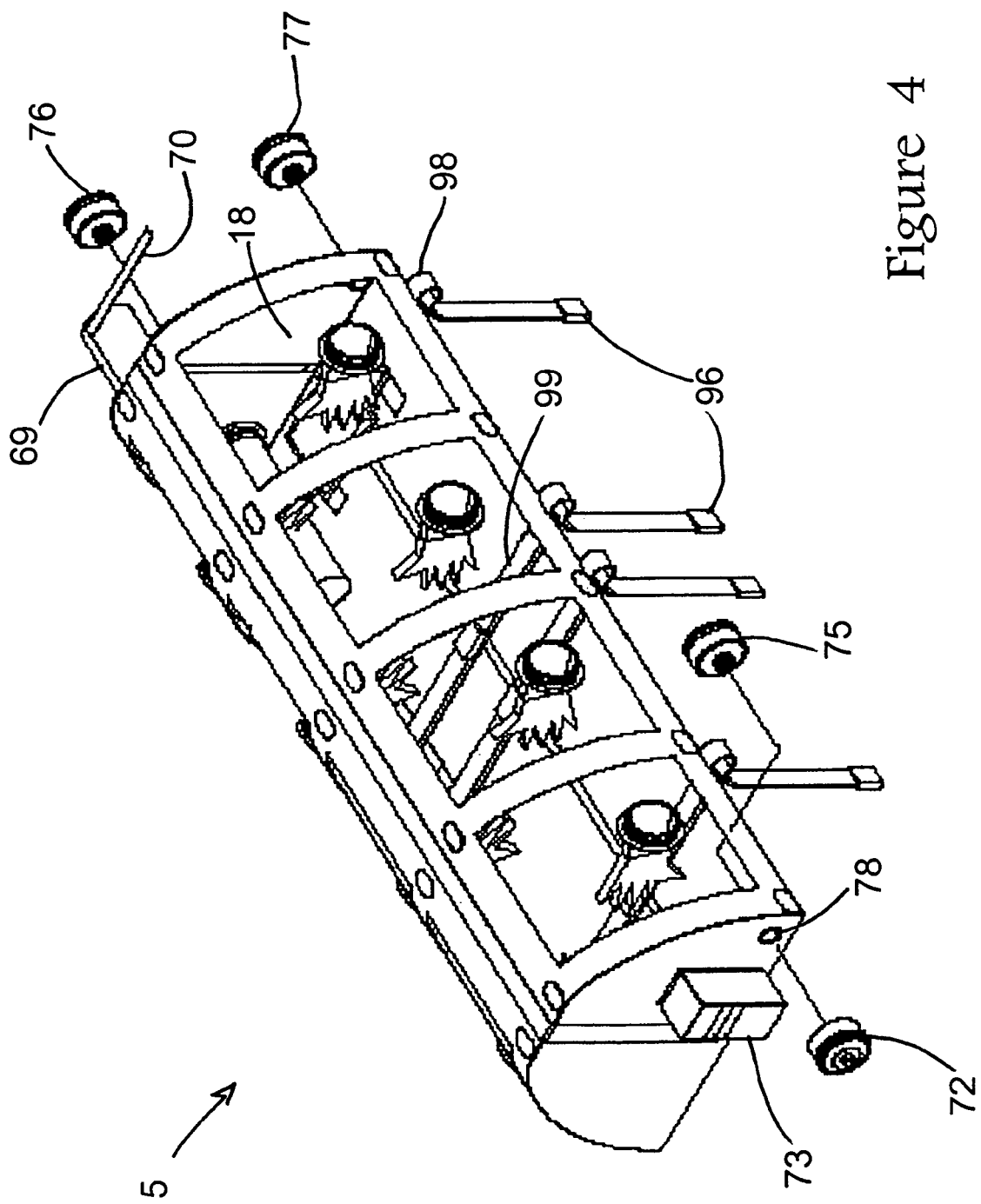
FIG. 4 shows a perspective view of the isolation pod of FIG. 1.

Referring to FIG. 4, several wide belts 96 may be provided in appropriate positions under the bottom sheet 15 to provide a means to lift the isolation pod 5, or to attach it to a stretcher or gurney. Handgrips, such as 98, on each side of the isolation pod 5 may be provided to enable staff to transport and maneuver a patient in the isolation pod 5. Furthermore, a plurality of internal restraining straps 99 may be disposed inside the main chamber 18 to hold a patient securely within the isolation pod 5.

In an alternate embodiment, an antechamber 86 (FIGS. 1 and 2) having additional high efficiency filters 88, 89 may be disposed on an end of the isolation pod 5. Such filters 88, 89 may be HEPA filters for filtering particulate, OVAG filters for filtering organic vapor, acid, or gas, or combinations of HVAC and OVAG. The antechamber 86 should be separately openable from the main chamber 18 to allow materials to be placed into the antechamber 86 without exposing the main chamber 18 to possible contamination from the outside environment. The materials can be sealed in the antechamber 86 and filters 76, 77 may clean any contaminated air that entered the antechamber 86 when it was opened. After a sufficient amount of time, the main chamber 18 can be opened to the antechamber 86 and the materials can be moved into the main chamber 18. The antechamber 86 may be provided with glove ports and gloves (not shown) to facilitate moving the materials between the main chamber 18 and the antechamber 86. If an antechamber 86 is provided, then the second bottom sheet 81, if provided, should preferably extend to the end of the antechamber 86.

Preferably, the isolation pod 5 is provided with at least one pass-through sleeve 100 that may be attached to an end panel 21, 22, 23, 24 to allow instruments or equipment to enter the main chamber 18. The pass-through sleeve 100 may open on the attached end and releasably sealed on the remaining, unattached end. Alternatively, a separate filter may be provided in a removably end cap that selectively opens and closes pass-through sleeve 100. A strap having hook-and-loop fasteners, similar to strap 70, may be used to seal the pass-through sleeve 100 to maintain the sleeve 100 closed. Other means to releasably close the sleeve 100 may be used. Objects to be passed into the main chamber 18 are placed into the sleeve 100. Using one of the gloves 65, an operator outside the enclosure 8 can squeeze the sleeve between the object and the open end to form a seal. The closure on the sealed end can be opened and the object removed inside the main chamber 18. The sleeve can then be resealed with the object remaining inside the enclosure 8.

In some embodiments, a sealed specimen sleeve 105 may be provided. The specimen sleeve 105 is preferably attached to a left or right side portion 11, 12 and has a sealed bottom. Optionally, the specimen sleeve may be provided a selectively openable bottom, such as by way of a zipper or similarly configured closure. A specimen from inside the main chamber 18 can be placed in the specimen sleeve 105 and sealed therein by heat sealing, adhesive, an additional zipper-type closure, or other appropriate means. A portion of the specimen sleeve 105 holding the specimen can then optionally be detached from the isolation pod 5 so that the specimen, while remaining sealed, can be transported to another location for testing, analysis, or other work. The specimen sleeve 105 should continue to maintain a seal with the enclosure 8.

All of the sleeves 69, 100, 105 described herein may be sealed to the isolation pod 5 by ultrasonic or radio frequency welding. Heat sealing, adhesives, or other conventional techniques may also be used.

The isolation pod 5 described herein can be used with a live patient to maintain a sealed environment in order to prevent the spread of contamination. In an alternate embodiment, the isolation pod 5 can be used to perform autopsies without compromising the environment.

The invention has been described with references to a preferred embodiment. While specific values, relationships, materials and steps have been set forth for purposes of describing concepts of the invention, it will be appreciated by persons skilled in the art that numerous variations and/or modifications may be made to the invention as shown in the specific embodiments without departing from the spirit or scope of the basic concepts and operating principles of the invention as broadly described. It should be recognized that, in the light of the above teachings, those skilled in the art can modify those specifics without departing from the invention taught herein. Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It is intended to include all such modifications, alternatives and other embodiments insofar as they come within the scope of the appended claims or equivalents thereof. It should be understood, therefore, that the invention may be practiced otherwise than as specifically set forth herein. Consequently, the present embodiments are to be considered in all respects as illustrative and not restrictive.

What is claimed is:

1. A collapsible patient isolation pod, comprising:
    a flexible enclosure, comprising:
        a first side and a second side, said first and second sides being substantially rectangular having two opposite long edges and two opposite short edges;
        a first end and a second end, said first and second ends being substantially semi-circular with a flat edge and a curved edge and having a split dividing both first and second ends in half, wherein
            the short edges of the first and second sides are attached to one half of the curved edge of the first and second ends, respectively; and
        a substantially rectangular bottom member having two opposite long edges and two opposite short edges that is attached on its long edges to a first long edge of each of the first and second sides, and attached on its short edges to the flat edge of the first and second ends;
    a plurality of spaced-apart ribs disposed within the enclosure configured to maintain the first and second sides vertically spaced apart from a patient received in the flexible enclosure;
    a plurality of spines operatively engaged between at least two of said spaced-apart ribs; and
    a closure configured to releasably close the second long edge of the first and second sides and to releasably close the split dividing both first and second ends.

2. The isolation pod of claim 1, wherein said flexible enclosure is at least partially transparent.

3. The isolation pod of claim 1, further comprising a plurality of spaced apart guide loops disposed on an inner surface of said first and second sides for engaging said plurality of ribs therein.

4. The isolation pod of claim 1, further comprising at least one port defined in the first end; and at least one port defined in the second end.

5. The isolation pod of claim 4, wherein at least one port is configured to be attached to a blower.

6. The isolation pod of claim 5, wherein said blower comprises a powered blower.

7. The isolation pod of claim 5, wherein said blower is electrically powered and includes a power source.

8. The isolation pod of claim 7, wherein said power source is portable.

9. The isolation pod of claim 7, wherein said power source comprises a battery.

10. The isolation pod of claim 4, wherein at least one port is configured to be attached to a filter.

11. The isolation pod of claim 10, wherein said filter is a HEPA filter, an OVAG filter, or combinations thereof.

12. The isolation pod of claim 4, further comprising a blower.

13. The isolation pod of claim 12, wherein said blower is portable.

14. The isolation pod of claim 12, wherein said blower comprises a powered blower.

15. The isolation pod of claim 12, wherein said blower is electrically powered and includes a power source.

16. The isolation pod of claim 15, wherein said power source is portable.

17. The isolation pod of claim 16, wherein said power source comprises a battery.

18. The isolation pod of claim 4, further comprising a filter.

19. The isolation pod of claim 18, wherein said filter is a HEPA filter, an OVAG filter, or combinations thereof.

20. The isolation pod of claim 4, further comprising a wall fitting having both internal and external threaded connections.

21. The isolation pod of claim 1, wherein the closure comprises a zipper.

22. The isolation pod of claim 1, wherein the closure comprises a hook-and-loop fastener.

23. The isolation pod of claim 1, further comprising a plurality of connection housings and wherein an end of each said plurality of spaced-apart ribs is slidably engaged in said connection housing.

24. The isolation pod of claim 23, wherein each end of said plurality of spines is slidably engaged in said connection housing.

25. The isolation pod of claim 1, further comprising:
a blower disposed on a first end; and
at least one filter disposed on a second end.

26. The isolation pod of claim 25, wherein said blower is portable.

27. The isolation pod of claim 25, wherein said blower comprises a powered blower.

28. The isolation pod of claim 27, wherein said blower is electrically powered and includes a power source.

29. The isolation pod of claim 28, wherein said power source is portable.

30. The isolation pod of claim 28, wherein said power source comprises a battery.

31. The isolation pod of claim 25, wherein said blower in configured to evacuate air from said flexible enclosure.

32. The isolation pod of claim 31, further comprising a filter disposed within said flexible enclosure at the inlet to said blower.

33. The isolation pod of claim 32, wherein said filter is a HEPA filter, an OVAG filter, or combinations thereof.

34. The isolation pod of claim 25, wherein said blower in configured to blow air into said flexible enclosure.

35. The isolation pod of claim 34, further comprising a filter disposed at the inlet to said blower.

36. The isolation pod of claim 35, wherein said filter is a HEPA filter, an OVAG filter, or combinations thereof.

37. The isolation pod of claim 25, wherein said filter is a HEPA filter, an OVAG filter, or combinations thereof.

38. The isolation pod of claim 1, further comprising:
an antechamber, comprising:
a third end, being substantially semi-circular with a flat edge and a curved edge and having a split dividing said third end in half, wherein
said third end is positioned such that said second end is between said first end and said third end, and wherein said first and second sides are sufficiently long to connect to said third end; and
the short edges of the first and second sides, opposite said first end are attached to one half of the curved edge of said third; and
said closure is configured to releasably close the split dividing said third end.

39. The isolation pod of claim 38, further comprising:
at least one filter disposed on said third end.

40. The isolation pod of claim 39, wherein said filter is a HEPA filter, an OVAG filter, or combinations thereof.

41. The isolation pod of claim 1, further comprising:
at least one specimen sleeve disposed on a side of said isolation pod.

42. The isolation pod of claim 41, wherein said at least one sleeve is sealed on a bottom thereof.

43. The isolation pod of claim 41, wherein said at least one sleeve is configured to hold a specimen therein to be sealingly removed from said isolation pod while maintaining said isolation pod environmentally sealed.

44. The isolation pod of claim 1, further comprising:
at least one sleeve disposed on an end of said isolation pod.

45. The isolation pod of claim 44, wherein said at least one sleeve is releasably closed on an end thereof.

46. The isolation pod of claim 44, said at least one sleeve further comprising a closure strap to releasably close said sleeve.

47. The isolation pod of claim 44, wherein said at least one sleeve is operatively engaged with said isolation pod and adapted to enable items to be passed into or out of said isolation pod while maintaining said isolation pod environmentally sealed.

48. A collapsible patient isolation pod, comprising:
a flexible enclosure, comprising:
a first side and a second side, said first and second sides being substantially rectangular having two opposite long edges and two opposite short edges;
a first end and a second end, said first and second ends being substantially semi-circular with a flat edge and a curved edge and having a split dividing both first and second ends in half, wherein
the short edges of the first and second sides are attached to one half of the curved edge of the first and second ends, respectively; and
a substantially rectangular bottom member having two opposite long edges and two opposite short edges that is attached on its long edges to a first long edge of each of the first and second sides, and attached on its short edges to the flat edge of the first and second ends;
a plurality of spaced-apart ribs disposed within the enclosure; and
a plurality of spines operatively engaged between at least two of said spaced-apart ribs, and
a blower disposed on a first end;
at least one filter disposed on a second end; and
a closure configured to releasably close the second long edge of the first and second sides and to releasably close the split dividing both first and second ends.

49. The isolation pod of claim 48, wherein said flexible enclosure is at least partially transparent.

50. The isolation pod of claim 48, wherein said blower is portable.

51. The isolation pod of claim 48, wherein said blower comprises a powered blower.

52. The isolation pod of claim 48, wherein said blower is electrically powered and includes a power source.

53. The isolation pod of claim 52, wherein said power source is portable.

54. The isolation pod of claim 52, wherein said power source comprises a battery.

55. The isolation pod of claim 48, wherein said blower in configured to evacuate air from said flexible enclosure.

56. The isolation pod of claim 55, further comprising a filter disposed within said flexible enclosure at the inlet to said blower.

57. The isolation pod of claim 56, wherein said filter is a HEPA filter, an OVAG filter, or combinations thereof.

58. The isolation pod of claim 48, wherein said blower in configured to blow air into said flexible enclosure.

59. The isolation pod of claim 58, further comprising a filter disposed at the inlet to said blower.

60. The isolation pod of claim 59, wherein said filter is a HEPA filter, an OVAG filter, or combinations thereof.

61. The isolation pod of claim 48, wherein said filter is a HEPA filter, an OVAG filter, or combinations thereof.

62. The isolation pod of claim 48, wherein the closure comprises a zipper.

63. The isolation pod of claim 48, wherein the closure comprises a hook-and-loop fastener.

64. A method of transporting a body in a protective environment, comprising the steps of:
   1) providing a flexible enclosure, comprising:
      a flexible enclosure, comprising:
         a first end and a second side, said first and second sides being substantially rectangular having two opposite long edges and two opposite short edges;
         a first end and a second end, said first and second ends being substantially semi-circular with a flat edge and a curved edge and having a split dividing both first and seconds ends in half, wherein the short edges of the first and second sides are attached to one half of the curved edge of the first and second ends, respectively; and
         a substantially rectangular bottom member having two opposite long edges and two opposite short edges that is attached on its long edges to a first long edge of each of the first and second sides, and attached on its short edges to the flat edge of the first and second ends;
      a plurality of spaced-apart ribs disposed within the enclosure configured to maintain the first and second sides vertically spaced apart from a patient received in the flexible enclosure;
      a plurality of spines operatively engaged between at least two of said spaced-apart ribs;
      a blower disposed on the first end;
      at least one filter disposed on the send end; and
      a closure configured to releasable close the second long edge of the first and second sides and to releasably close the split dividing both first and second ends of said enclosure; and
   2) using said blower to establish airflow within said enclosure, generally along the longitudinal axis of said enclosure.

65. The method of claim 64, further comprising the steps of:
   3) placing a body in said enclosure; and
   4) aligning said body such that the head is nearest the end where air enters the enclosure and the feet are nearest the end where air exits the enclosure.

66. The method of claim 65, said enclosure further comprising restraining straps to releasably hold said body within said flexible enclosure.

67. The method of claim 65, wherein said spaced-apart ribs maintain the first and second sides spaced apart from the body received in the flexible enclosure.

68. The method of claim 64, wherein said blower comprises a powered blower.

69. The method of claim 64, wherein said blower is electrically powered and includes a power source.

70. The method of claim 69, wherein said power source is portable.

71. The method of claim 69, wherein said power source comprises a battery.

72. The method of claim 64, wherein said blower in configured to evacuate air from said flexible enclosure.

73. The method of claim 72, said enclosure further comprising a filter disposed within said flexible enclosure at the inlet to said blower.

74. The method of claim 73, wherein said filter is a HEPA filter, an OVAG filter, or combinations thereof.

75. The method of claim 64, wherein said blower in configured to blow air into said flexible enclosure.

76. The method of claim 75, further comprising a filter disposed at the inlet to said blower.

77. The method of claim 76, wherein said filter is a HEPA filter, an OVAG filter, or combinations thereof.

78. The method of claim 64, wherein said filter is a HEPA filter, an OVAG filter, or combinations thereof.

79. The method of claim 64, wherein said flexible enclosure is at least partially transparent.

* * * * *